United States Patent [19]

Lawrence

[11] 4,431,414
[45] Feb. 14, 1984

[54] DENTAL SYRINGE FOR FILLING CAVITIES IN TEETH

[76] Inventor: John S. Lawrence, Rte. 896 & Peacedale Rd., Kemblesville, Pa. 19347

[21] Appl. No.: 342,505

[22] Filed: Jan. 25, 1982

[51] Int. Cl.³ .............................................. A61C 5/04
[52] U.S. Cl. ..................................................... 433/90
[58] Field of Search ............................ 433/90, 89, 83; 222/333, 137

[56] References Cited

U.S. PATENT DOCUMENTS

| 3,451,135 | 6/1969 | Moller | 433/90 |
| 3,638,314 | 1/1972 | Lopez | 433/90 |
| 4,260,077 | 4/1981 | Schroeder | 222/137 |

FOREIGN PATENT DOCUMENTS 619242  3/1949  United Kingdom .................. 433/90

Primary Examiner—Robert Peshock

[57] ABSTRACT

A dental syringe for filling cavities in teeth with dental filling materials and can be dispensed into a tooth cavity in measured in increments of all or a portions of one or two-predetermined quantities of filling material. The syringe is composed of an elongated body barrel having two hollow, contiguous parallel shafts and a disposable chamber removably attached to the barrel and having two hollow contiguous parallel shafts which are coextensive and continuous in precise axial dimensions as the shafts in the barrel.

10 Claims, 12 Drawing Figures

DENTAL SYRINGE FOR FILLING CAVITIES IN TEETH

BACKGROUND OF THE INVENTION

1. Field of the Invention

My invention relates generally to dental instruments, and more particularly to an apparatus of relatively simple construction and operation for simplistically loading and selectively dispensing into a tooth cavity measured increments of all or a portion of one or two pre-determined quantities of a dental filler material, while maintaining sterility of the part of the apparatus which is introduced into a patient's mouth and avoiding malfunctioning of the apparatus due to the filler's clogging its passageways.

2. Background of the Prior Art

Tooth cavities are filled with various filler materials, most often an amalgam of mercury and silver or mercury and a mixture of silver and tin, and/or copper, and/or zinc. The amalgam preferably is mixed in individual units called "spills". The units most commonly used by the dentist contain either one, two or three spills (the respective quantities consisting of 500 mg., 1000 mg., or 1500 mg). As a rule, it requires up to two spills to fill the average tooth cavity.

The amalgam is extruded from a dental amalgam carrier into a tooth cavity. The period during which the amalgam remains in a plastic state so that it can be extruded from the carrier into a tooth cavity, and compacted in the cavity so as to expel any trapped air and excess mercury is about 5 minutes. Normal dental practice is to introduce small increments of amalgam into the cavity initially, each time tamping the material into all of the cavity's crevices, and then add larger quantities until the cavity is entirely filled.

The properties of amalgam are unique. Being a eutectic mixture, the material has the ability to be transferred from a plastic, semi-solid state to a final solid state in which it can withstand compressive forces over 65,000 psi. The effective working time from the moment the amalgam is completely mixed until it is initially set is approximately three or four minutes. In that time the material passes through three stages, as follows:

(1) Plastic, semi-solid with a high degree of workability;

(2) Crumbling mixture which is of course texture and has a low degree of workability; and (3) Set, gradually changing from a very low degree of workability to no workability at all.

Within a time frame of 1-2 minutes the mixed amalgam must be placed within the tooth cavity, then compacted and condensed so as to drive off any excess mercury.

The first stage lasts for about 45 seconds to 1½ minutes. It is essential that the amalgam be transferred from the vessel in which it is mixed to the tooth cavity in the shortest possible period of time. In the past this transfer was done by the dentist using his fingers. Later, tubular or cylindrical amalgam carriers were substituted for the fingers.

Some of the earlier forms of amalgam carriers and dispensers were designed to load the carriers through the ends of the instruments' cylindrical or tubular barrel from which the amalgam later is expelled into a tooth cavity. In other words, the material is loaded and dispensed through the same end of the instrument. Such designs have inherent limitations as to the quantities of amalgam which can be carried by the instrument, for if the diameters of the barrels are increased to any significant degree to accommodate more amalgam material the cross-sections of the ends of the barrels would be too large to effectively insert the amalgam into the much smaller diameter of a tooth cavity. The alternative of lengthening the barrels to hold more amalgam is not satisfactory as it would tend to increase the likelihood of the amalgam losing its plasticity and clogging the instrument barrel, in addition to making it next to impossible to load the amalgam mix into the barrel.

A prior art improvement over the "front end" loading design is the provision of a magazine or amalgam-containing chamber situated behind the discharge end of the amalgam dispenser. A plunger is provided in this construction by which the dentist is able to push amalgam out of the magazine through a nozzle from which the amalgam is ejected into a tooth cavity. The magazine is so constructed as to resemble two parallel shafts, but with only one discharge nozzle and with a single plunger. To line up the plunger so that it is axially movable in first one shaft and then the other it is necessary to move the chamber back and forth. This design has certain inherent disadvantages in that the movement of the chamber, the double movement which must be imparted to the plunger, the limitation of the amount of amalgam in the magazine to a single charge, all can cause the instrument's user problems in its operation. In addition, the device's nozzle can become clogged with amalgam, and when this occurs it becomes so difficult to remove the hardened amalgam from the nozzle that quite often the instrument has to be discarded.

The limitation of prior art devices as to the quantity of amalgam which they can carry is a troublesome problem to the dentist. The amount of amalgam which has to be prepared for introduction into a tooth cavity is a relatively large mass in comparison with the mass of filling material that actually can be introduced by the carrier to the tooth cavity at any instant. If a carrier with a magazine having a single chamber is employed, putting all of the required amount of the amalgam mix into the carrier chamber at one time does not solve the problem since it is not possible to compress amalgam from a chamber of larger diameter (i.e. from a larger mass of amalgam) into a carrier exit opening of small diameter (i.e. to a smaller mass of amalgam). This is due to the physical nature of the material. It should be noted that the smaller diameter, which is the diameter of the nozzle's working tip of the instrument that actually is inserted into the tooth cavity, generally cannot be useful if it is any larger than 3.5 mm.

Still another prior-art amalgam carrier provides two plungers situated parallel to one another and each movable axially the length of the apparatus, one for dispensing amalgam from a magazine into a discharge nozzle and the other for expelling the amalgam out of the nozzle and into a tooth cavity. This device is impractical because the amount of material expressed from the nozzle in relationship to that contained in the magazine, and the time required for all of the material to be discharged, are both factors that cause the material in the instrument to become so hardened as to make it difficult to clean the instrument or reload the same instrument quickly enough for re-use by the dentist on the same patient.

In my own dental practice I have seen and/or used one variation or another of these and other prior art devices for conveying dental amalgam to a patient's tooth, and have found them to have numerous shortcomings. It was in seeking to overcome these shortcomings that I devised my present invention which I shall now describe with reference to the attached drawings.

SUMMARY OF THE PRESENT INVENTION

My novel dental syringe basically comprises: (a) an elongated body member or barrel having two hollow, contiguous, parallel shafts extending throughout its length, either cylindrical or rectangular in shape; (b) a disposable magazine or chamber removably attached to the barrel and having two hollow, contiguous, parallel shafts which are coextensive and continuous in precise axial alignment with and having essentially the same cross-sectional dimensions as the shafts in the barrel; (c) a nozzle having a working tip for directing amalgam ejected from the chamber into a tooth cavity, and having two hollow, contiguous parallel shafts coextensive and continuous in precise alignment with and having essentially the same cross-sectional dimensions as the shafts in the chamber; (d) a collar borne by the barrel for supporting and anchoring in place the chamber and its attached nozzle; and (e) two plungers, each spring-loaded for independent reciprocal movement axially within its own enveloping shaft in the barrel.

The chamber has a cover which is hinged at one side along its length so that it may be conveniently opened to insert a charge of amalgam in the chamber. The under side of the cover is shaped so as to form one-half of the two continuous shafts that extend through the chamber, and when the cover is in its closed position those halves mate with matching halves of the shafts in the fixed portion of the chamber. When the shafts are cylindrical in shape the portions of the shafts in the cover and in the chamber's fixed portion are hemispheric in cross-section, and when the cover is in its closed position the effect is to produce two hollow, contiguous, parallel tubes.

Attached to and extending from the chamber is the nozzle essentially comprising two contiguous shafts (each being tubular in shape in cases where the shafts in the chamber are tubular) which are coextensive and continuous in precise alignment with and having essentially the same cross-sectional dimensions as the shafts in the chamber. The nozzle is preferably J-shaped so as to facilitate placement of its working tip into a tooth cavity.

The two rods or plungers, each with a convenient finger rest at one end, are mounted for axially reciprocal movement, one plunger operating in and throughout one of the contiguous shafts in the barrel and chamber and extending into and through the entire nozzle, and the other plunger operating in and throughout the other shaft in the barrel, chamber and nozzle. The two plungers, which optionally may have a circular or rectangular cross-section, are spring-loaded and located in the barrel so that before use of the apparatus their finger rests protrude their maximum distance of travel outside the barrel, and pressure on those rests is required in order to move the plungers from their initial positions in the barrel, but not in the chamber, to gradually successive positions in which they extend through the chamber and through the entire nozzle.

Before the syringe is put to use, the cover in the detached chamber is opened, amalgam is placed inside the chamber, and the cover is closed. The chamber is then fitted into the collar so that the shafts extending through the body are aligned with the shafts in the chamber. Closing of the cover causes the amalgam to be compressed and spread out to take the shape of the two contiguous shafts. When the shafts are of cylindrical design the amalgam fills them so as to take on a tubular form and is extruded in that form from the syringe; when the shafts are rectangular in cross-section the extruded material is also rectangular in cross-section. The dentist using the syringe can selectively apply pressure on each of the plungers to cause them to move axially, either one after the other or together, so as gradually to express the amalgam out of the chamber and through the nozzle into a tooth cavity. Release of the pressure on the plungers causes them to move backwards away from the nozzle and chamber under the influence of the springs by which they are movably attached to the barrel.

As the foregoing description makes clear, the unique and foremost feature of my invention is that a total required charge of amalgam can be loaded into the chamber and then expressed either wholly or in part into the tooth cavity, following which the chamber and its attached nozzle can then be detached from the main body of the instrument and replaced by a newly loaded chamber and nozzle.

DESCRIPTION OF THE PREFERRED EMBODIMENT

Figure 1:
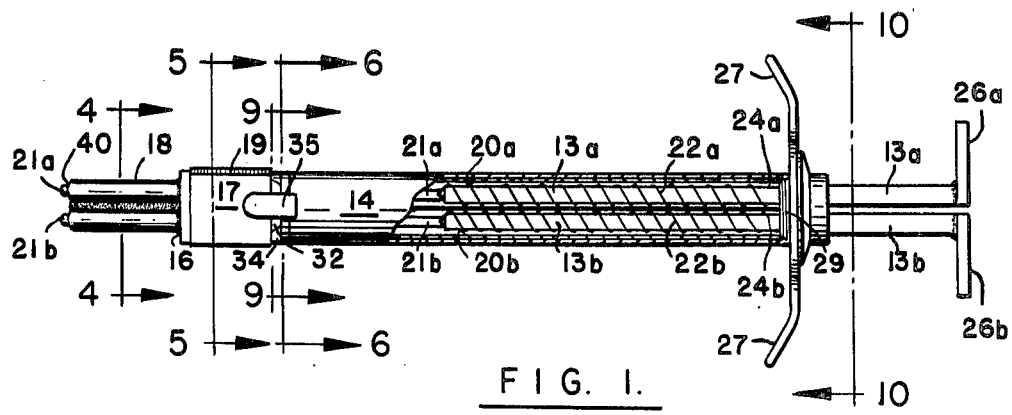
FIG. 1 is a top plan view of a preferred embodiment of the entire novel syringe, with a piece of the main body's wall broken away to expose the spring-loaded plungers each located individually in a corresponding one of the shafts extending through the body.
Figure 2:
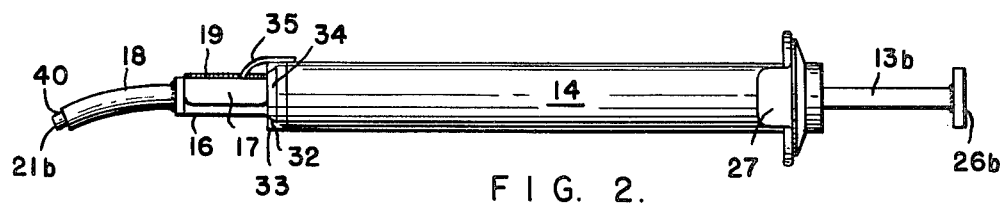
FIG. 2 is a side elevation of the FIG. 1 device, which has been turned 90° on its axis so as to show the J-shaped nozzle, the depending flange on the chamber's cover, and the collar which supports the chamber and keeps it in place when in its closed position.
Figures 3, 7, 8:
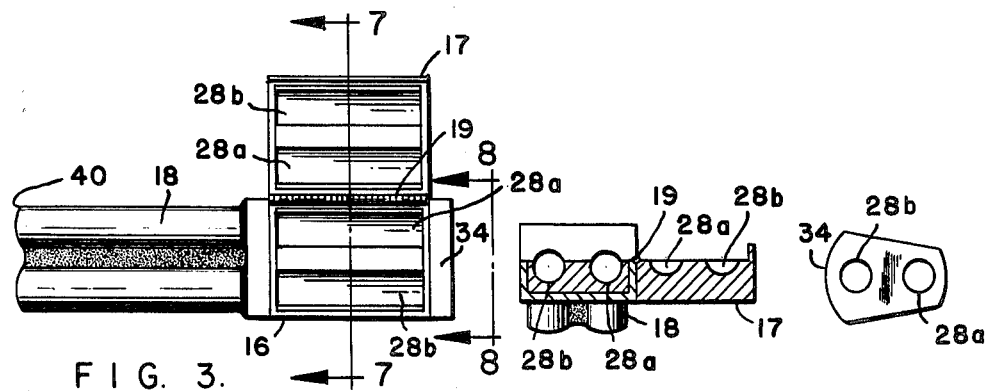
FIG. 3 is an axial elevation view of the nozzle and chamber portions of the FIG. 1 embodiment, with the plungers removed and the cover of the chamber in its fully open position.
FIG. 7 is a view taken from line 7—7 of FIG. 3 to show in cross-section the chamber with its cover in the fully open position.
FIG. 8 is a partial view taken from line 8—8 of FIG. 3 to show only the wedge-shaped end of the chamber which fits into an accommodating wedge-shaped end of the collar that supports and secures the chamber to the body.
Figures 4, 5, 6, 9:
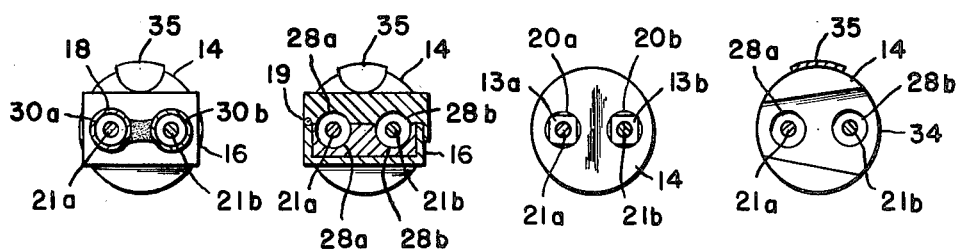
FIG. 4 is a partial view taken from line 4—4 of FIG. 1 to show in cross-section only the nozzle with the parallel shafts and plungers extending therethrough.
FIG. 5 is a partial view taken from line 5—5 of FIG. 1 to show in cross-section only the closed chamber with the plunger rods each contained in a separate one of the shafts extending through the chamber.
FIG. 6 is a partial view taken from line 6—6 of FIG. 1 to show in cross-section only the barrel with the plunger rods each contained in a separate one of the shafts extending through the barrel.
FIG. 9 is a partial view, taken from line 9—9 of FIG. 1, to show the wedge-shaped end of the collar into which fits the wedge-shaped end of the chamber shown in FIG. 8.
Figure 10:
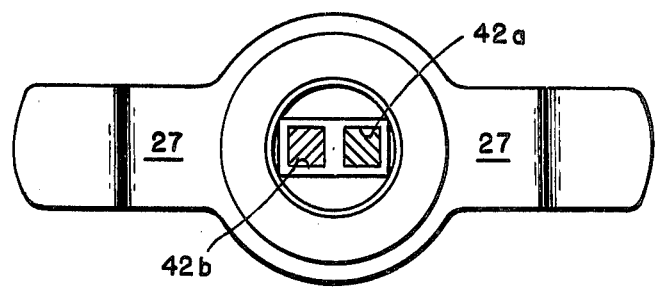
FIG. 10 is a view taken from line 10—10 of FIG. 1, to show finger-holds which the user grips with his fingers as his thumb depresses the plungers, and also showing parallel rectangular tubes inside the entrance to the syringe which serve to guide the rectangular plungers and hold the plungers so as to minimize their cocking as they are depressed.

As best seen in FIGS. 1, 2 and 3, the preferred embodiment of my invention is a syringe with two dispensing plungers 13a and 13b, a body member or barrel 14, and a removable magazine or chamber 16 from which extends an amalgam extruding nozzle 18 having a working tip 40. Two parallel, hollow shafts 20 extend axially through the entire barrel. These shafts may be cylindrical so as to constitute two contiguous tubes, although other shapes such as a rectangular cross-sectional configuration could be employed. In each of the shafts 20a and 20b one of the plungers 13a or 13b is spring-loaded by means of coiled springs 22a and 22b whose ends are respectively secured to the inside wall of the chamber as at 24a and 24b. Finger rests 26a and 26b are provided at the ends of the plungers external to the chamber; they serve as convenient means for the user of the syringe selectively and gradually, with the pressure of his thumb, to depress the plungers either singly or doubly. This allows for dispensing all or a part of the full charge of amalgam without requiring re-loading while filling a tooth. In so depressing the plungers the force provided by springs 22, which serves to keep a considerable length of the plungers out of the barrel until sufficient pressure is applied to the plungers, is overcome and the springs are compressed. The ends of the plungers inside the barrel are thereby caused to travel axially through shafts 28a and 28b in chamber 16 and through shafts 30a and 30b (see FIG. 7) and all the way through nozzle 18. Optionally, instead of providing two parallel shafts through the entire barrel it is possible to provide two parallel and contiguous shafts extending from the end of the barrel farthest from the chamber a sufficient distance part way into the barrel to serve as supports and guides for the axial movement of the plungers. Two such guide-supports 42a–42b are shown in FIG. 10. Their rectangular cross-sections are dimensioned to enable the plungers to slide through them without difficulty, and at the same time to prevent cocking of the plungers in the support-guides.

Figure 11:
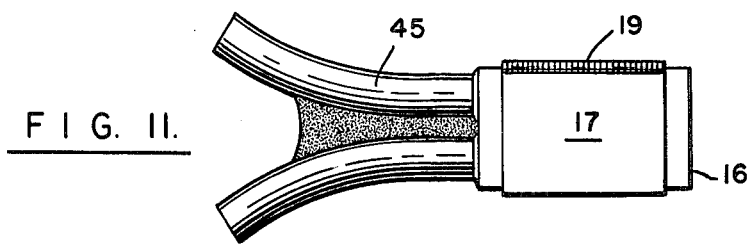
FIG. 11 is a top plan view of an alternate, Y-shaped nozzle with its attached chamber.
Figure 12:
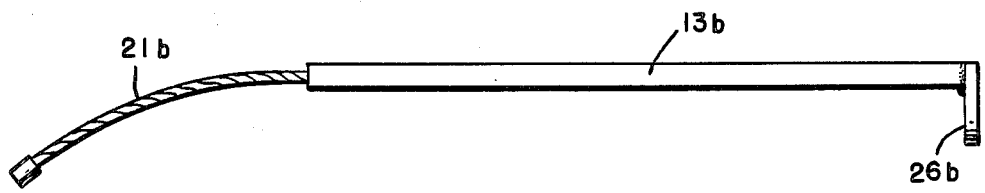

Plungers 13a and 13b can optionally be made entirely of rigid metallic or plastic material. Preferably, the portions which extend only through the barrel can be of rigid composition with the remaining portions 21a–21b (FIGS. 1,2 and 12) that are to extend through the chamber and the nozzle being sufficiently flexible so as to follow the curvature of shafts 30a and 30b in the J-shaped nozzle 18 (FIG. 2) or the Y-shaped nozzle 45 (FIG. 11).

Barrel 14 has, at its end nearest the plunger finger rests, a flange 27 extending laterally which serves as a finger grip that enables the syringe user to grip the barrel more comfortably and securely when operating the instrument. The flange preferably is threadedly attachable to the barrel, as at 29, and is removable to facilitate attachment of the free ends of springs 22a and 22b to the barrel's interior wall as indicated at 24a and 24b. The other ends of the springs preferably are attached to the junction of the plungers' rigid portions 13a–13b and their flexible portions 21a–21b. The flange 27 serves the additional purpose of holding and guiding the plungers in their axial movements. At the barrel end longitudinally farthest from the finger rests a collar portion 32 is provided which is shaped so as to function as one part of a two-part locking mechanism for removably securing the chamber 16 to the barrel. The other part of the locking mechanism is the portion 34 of the chamber. The collar 32 serves to receive chamber portion 34 in inter-fitting, mating relationship. In the optional design shown in the drawings this mating relationship is achieved by making the protruding chamber portion 34 wedge-shaped (see FIG. 8) and the collar portion 32 has a complimentary wedge-shaped recess 33. Another optional design (not shown) is a keying arrangement of parts 32 and 34 by which, with a twist in a clockwise or counterclockwise direction, those parts can be placed in or withdrawn from a securely fastened, interlocking relationship.

Chamber 16 has a cover 17 which is pivotably secured to the chamber by a hinge 19. Although the hinged attachment optionally could be at one end of the chamber, by attaching it in the illustrated position the cover serves the additional function of helping to retain the amalgam spill as it is inserted in the chamber. The under side of the cover is fashioned so as to serve as much as about one-half of the two, parallel, contiguous shafts 20a and 20b extending longitudinally therethrough (see FIGS. 2,4,5 and 6). The fixed part of the chamber, on which the cover rests when in the closed position, is fashioned so as to serve as the mating remainder of the two shafts 20a and 20b. As a result, when the cover is in its closed position the chamber shaft portions 28a and 28b on the under side of the cover mate with the corresponding shaft portions 28a and 28b on the fixed part of the chamber (see FIGS. 3 and 7) to complete the two tubes or shafts that extend through the chamber. Those chamber shafts are in precise alignment with the shafts 20a and 20b, respectively, in the barrel so that in effect the barrel and the chamber have two continuous shafts extending longitudinally through both of them.

The cover 17 can be secured to chamber 16 in several different ways. One obvious expedient is to provide a simple fastening means (not shown) such as a detent on the cover which engages a recess therefor in the body of the chamber. Another expedient (not shown) is to dimension the outer circumference of the chamber so that the chamber and a part of the cover in closed position fit some distance inside the barrel 14. When so fitted the engagement of the two-part locking mechanism 32–34 causes the cover to be held securely in its closed position by the barrel's interior wall. In the illustrated mode a chamber cover locking member 35 is provided; it is a rigid piece of sheet metal attached at one end to barrel 14 and/or collar 32, which is bent to fit against the cover and prevent it from being opened.

The chamber could be fabricated from a variety of materials, metallic or non-metallic. Since in practice it will most preferably be a disposable item, making it from an inexpensive plastic substance probably will be the most economical design. The shape of the chamber, and of the shafts passing through them can vary in design in accordance with the designer's choice. For example, the chamber is shown as having a rectangular configuration in FIGS. 1–5, but it could just as conveniently be made in a cylindrical form. The shafts in the chamber could optionally be designed to have a tubular construction or a rectangular configuration. Of course, the shafts in the barrel and nozzle would have to be essentially of the same shape and of the same cross-sectional dimensions as in the chamber, and would have to be able to accommodate the plungers 13 and their flexible portion 27 for axial movement therethrough.

Nozzle 18 is shown attached as a unitary part of the chamber and is disposed of when the chamber is discarded. The nozzle could, of course, optionally be made as a separate item which would be removably attachable to the chamber and detachable for disposal. Furthermore, the nozzle could, if desired, be constructed in a linear configuration, (not shown) and would appear as a straight line extension of the barrel and the chamber. Alternatively, the configuration could be gradually curved in a J-shape (FIGS. 1 and 2), or a Y-shape (FIG. 11). The different shapes could provide the user with a choice to suit his preference and convenience.

As is evident from the foregoing description of the component parts of the unique syringe, the apparatus makes it possible to transfer a mix of amalgam from the mixing vessel to the patient's tooth cavity in one simple, smooth operation. The amalgam is loaded into the chamber 16, the cover 17 is closed, and chamber is engaged and interlocked with the barrel 14, as described. Either before or after the chamber is fitted to the barrel the plungers are inserted in the shafts throughout the length of the barrel. The user of the syringe then applies pressure selectively or consecutively on the finger rests 26a or 26b, thereby causing the plungers 13a and 13b to express as much amalgam as desired out of the chamber, first through one shaft 20a-28a and then through the other shaft 20b-28b in nozzle 18, and out from the syringe working tip 40 into the tooth cavity.

While the operator is doing this an assistant can, if desired, load another chamber with another charge of amalgam. As soon as the operator decides there is need for the second charge of amalgam the first chamber can readily be detached from the barrel and either disposed of or laid aside for cleansing and re-sterilization, and the second chamber can be attached and locked in place to the barrel in an instant. This rapid change of chambers and their attached nozzles makes it possible for the operator to add the second charge of amalgam to the patient's tooth so quickly after the first charge that the effect is almost the same as if the two charges were one. Yet, by making it possible to use two separate charges, which could even be mixed separately in time with the second charge being mulled in the mixing vessel while the first charge is being inserted in the syringe and then in the patient's tooth cavity, better control is maintained over the plasticity and workability of each charge. The net result is that there is less likelihood of the amalgam hardening prematurely and clogging the syringe, especially its nozzle. If clogging were to occur it would only affect the disposable nozzle and chamber which can be removed and replaced. The main parts of the instrument (the barrel and the plungers) would be unaffected.

When the operator feels that sufficient amalgam has been inserted into the tooth, so that the amalgam needs to be tamped in place and inspected, release of the pressure on the plunger rod finger rests 26 will cause the plungers to retract into the nozzle, chamber and the barrel under the influence of springs 22. This serves to keep unused portion of the amalgam charge from being exposed outside the syringe's working tip 40, thereby minimizing any chance of the amalgam becoming contaminated. Likewise, when the used chamber and nozzle are to be removed in order to substitute a newly charged chamber and nozzle the plungers need first to be allowed to become fully retracted into the barrel. This avoids having the plungers' free ends exposed to contaminants in the air while the exchange of chambers is taking place.

Although the various advantages of the novel syringe over prior art devices will be obvious from the foregoing description of the illustrated and optional modes of the apparatus, some of the more significant ones will be mentioned for emphasis. In general, my invention provides, in comparison with comparable prior art devices, increased capacity, loading efficiency, ease of maintaining sterility, minimization of clogging due to premature hardening of the amalgam, and much longer useful life of the major parts of the apparatus as the working parts that are used repeatedly are relatively few and trouble-free. The syringe's chamber can readily hold a two-spill charge of mixed amalgam, which can be divided in two parts for ready discharge of one-half the charge at a time in desired increments and then readily followed by discharge of the remainder. If a second two-spill charge is needed, that can be done with the same basic instrument simply by exchanging a fully charged chamber and nozzle for a discharged chamber and nozzle in just an instant.

When the syringe is not in use, it can be readily disassembled and the barrel, plungers and springs sterilized. If the chamber and nozzle are made of inexpensive materials they can be discarded. The parts of the apparatus being so few in number, so easily made and maintained, an additional overall advantage is that the device is highly economical as well as a significant improvement in the facile use of such instruments by the dentist.

I have pointed out and illustrated what I, as a practicing dentist, believe to be the preferred embodiment of my invention and its advantages over prior art devices. To those skilled in the art it will be apparent that other modifications to my invention or structural changes in the device as shown and described can be made without departing from its spirit or scope in any way. For example, although I have illustrated and described my unique instrument in its preferred embodiment consisting of two plungers and two accommodating shafts through the barrel, chamber and nozzle, it should readily be apparent that an obvious variation thereof would be to have a single plunger and only one shaft through the barrel, chamber and nozzle. I therefore believe that the reasonable metes and bounds of my invention are only those defined by the claims at the end of this specification.

I claim:

1. A dental syringe for filling cavities in teeth with dental filling materials, comprising:
   an elongated barrel having at least one shaft extending axially therethrough;
   replaceable chamber having an open wall through which dental filling material may be inserted, said chamber being removably attached to one end of the barrel just prior to use of the syringe and having at least one shaft extending axially therethrough which is in axial alignment with and in cross-section of substantially equal dimensions to the minimum cross-sectional dimensions of the shaft in the barrel;
   a cover attachable to said chamber so as selectively to close the open wall and thereby retain therein a charge of dental filling material placed in the chamber immediately prior to use of the syringe and until the charge is expressed therefrom;

a nozzle extending from said chamber in the opposite direction from the barrel, said nozzle having at least one shaft which is essentially continuous with and in cross section of substantially equal dimensions to the shaft in the chamber;

a collar interfitting between said barrel and chamber for supporting and securely anchoring the chamber and its attached nozzle in relation to said barrel so that the shafts in the barrel and chamber are in axial alignment with each other throughout use of the syringe; and at least one plunger located in and axially movable throughout the shafts in the barrel, chamber and nozzle so as selectively to force dental filling material out of the chamber and out through the nozzle.

2. A dental syringe for filling cavities in teeth with dental filling materials, comprising:

an elongated barrel having two hollow, contiguous, parallel shafts extending axially therethrough;

a replaceable chamber having an open wall through which dental filling material may be inserted, said chamber being removably attached to one end of said barrel just prior to use of the syringe and having situated in its wall opposite the open chamber wall essentially one half of longitudinally subdivided hollow, contiguous, parallel shafts which are substantially coextensive and continuous in axial alignment with and which have substantially the same cross-sectional dimensions as the minimum cross-sectional dimensions of the shafts in the barrel;

a cover attachable to said chamber so as selectively to close the chamber's open wall and thereby retain therein a charge of dental filling material placed in the chamber immediately prior to use of the syringe and until the charge is expressed therefrom, said cover having situated in its under side essentially one half of two longitudinally subdivided hollow, contiguous parallel shafts in mating relationship with the other shaft halves in said chamber;

a nozzle extending from said chamber and having a working tip for directing dental filling material from the chamber into a tooth cavity, said nozzle having two hollow, contiguous, parallel shafts extending throughout the length of the nozzle so as to be coextensive and continuous in axial alignment with and having substantially the same cross-sectional dimensions as the shafts in the chamber and the mated shafts in the chamber cover;

a collar interfitting between said barrel and chamber for supporting and securely anchoring in place the chamber and its attached nozzle so that the shafts in the barrel and chamber are secured in axial alignment with each other throughout use of the syringe; and two plungers, each located in and independently movable axially throughout a separate one of the shafts in the barrel and the coextensive shafts in the chamber and nozzle so as selectively to force dental material in the chamber out from the chamber and out from the nozzle.

3. A dental syringe according to claim 2, in which the nozzle is J-shaped.

4. A dental syringe according to claim 2, in which the nozzle is Y-shaped.

5. A dental syringe according to claim 2, in which the nozzle has a linear configuration in axial co-alignment with the chamber and barrel.

6. A dental syringe according to claim 2, in which the plungers each consist of a substantially rigid portion which can be moved axially throughout the length of the barrel and extending from that rigid portion a substantially flexible portion which can be moved axially throughout the length of the chamber and the nozzle.

7. A dental syringe according to claim 2, in which the plungers are each spring loaded so that each will yield upon application of compressive force to the plunger so as to cause it to move through the barrel and into the chamber and nozzle, but upon release of the compressive force will cause the plunger to move in the opposite direction away from the chamber and nozzle.

8. A dental syringe according to claim 2, in which the collar has a wedge-shaped recess in its end which is in abutment with the chamber and the abutting chamber surface has a wedge-shaped locking member which matingly interfits within the collar's recess, thereby serving to hold the chamber and barrel in proper axial alignment so that the shafts in the barrel and the corresponding shafts in the chamber are in coextensive, continuous axial relationship with each other.

9. A dental syringe according to claim 2, in which the barrel has attached thereto a chamber cover locking member that protrudes from the barrel and extends over and applies pressure to the outside surface of the chamber cover so as to retain the cover in its closed position when the chamber is in its interfitting, axially aligned position with the barrel.

10. A dental syringe according to claim 2, in which guide-supports are provided in the entrance to the interior of the barrel, at the end of the barrel which is farthest from the attached chamber, the guide-supports being dimensioned so as to enable the plungers to slide through them into the barrel's interior without difficulty and at the same time prevent cocking of the plungers in the guide-supports.

* * * * *